(12) United States Patent
Han et al.

(10) Patent No.: US 9,024,062 B2
(45) Date of Patent: May 5, 2015

(54) REACTOR AND PROCESS FOR PROPANE OXIDATION

(75) Inventors: Scott Han, Lawrenceville, NJ (US); Christopher Frick, Pottstown, PA (US); Daniel J. Martenak, Perkasie, PA (US)

(73) Assignee: Rohm and Haas Company, Philadelphia, PA (US)

( * ) Notice: Subject to any disclaimer, the term of this patent is extended or adjusted under 35 U.S.C. 154(b) by 126 days.

(21) Appl. No.: 13/994,976

(22) PCT Filed: Dec. 7, 2011

(86) PCT No.: PCT/US2011/063652
§ 371 (c)(1),
(2), (4) Date: Jun. 17, 2013

(87) PCT Pub. No.: WO2012/091865
PCT Pub. Date: Jul. 5, 2012

(65) Prior Publication Data
US 2013/0274509 A1    Oct. 17, 2013

Related U.S. Application Data

(60) Provisional application No. 61/428,056, filed on Dec. 29, 2010.

(51) Int. Cl.
*C07C 51/215*    (2006.01)
*B01J 8/06*    (2006.01)

(52) U.S. Cl.
CPC ............... *C07C 51/215* (2013.01); *B01J 8/067* (2013.01); *B01J 2208/00061* (2013.01); *B01J 2208/00212* (2013.01); *B01J 2219/002* (2013.01); *B01J 2219/00213* (2013.01)

(58) Field of Classification Search
None
See application file for complete search history.

(56) References Cited

U.S. PATENT DOCUMENTS

| | | |
|---|---|---|
| 5,380,933 A | 1/1995 | Ushikubo et al. |
| 6,005,121 A | 12/1999 | Ebner et al. |
| 6,180,825 B1 | 1/2001 | Lin et al. |
| 6,858,754 B2 | 2/2005 | Borgmeier |
| 7,304,014 B2 | 12/2007 | Cavalcanti et al. |
| 7,807,853 B2 | 10/2010 | Dieterle et al. |
| 2003/0065194 A1 | 4/2003 | Weiguuy et al. |
| 2007/0299278 A1 | 12/2007 | Hechler et al. |

FOREIGN PATENT DOCUMENTS

| | | |
|---|---|---|
| CN | 1771222 A | 5/2006 |
| EP | 0987057 A1 | 3/2000 |
| EP | 1436244 B1 | 5/2008 |
| EP | 1615870 B1 | 6/2008 |

*Primary Examiner* — Yevegeny Valenrod
(74) *Attorney, Agent, or Firm* — Whyte Hirschboeck Dudek S.C.

(57) ABSTRACT

The amount of propionic acid produced in the process of oxidizing propane to acrylic acid is reduced by using a reactor with a length/diameter ratio >10 and/or maintaining the difference between the target reaction temperature and the peak temperature within the reactor to less than 20° C.

5 Claims, No Drawings

REACTOR AND PROCESS FOR PROPANE OXIDATION

CROSS REFERENCE TO RELATED APPLICATION

The present application is the national phase of PCT Patent Application No. PCT/US2011/063652 filed Dec. 7, 2011, which claims priority to U.S. Provisional Application No. 61/428,056 filed Dec. 29, 2010, the entire content of which is incorporated by reference herein.

BACKGROUND OF THE INVENTION

1. Field of the Invention

This invention relates to propane oxidation. In one aspect the invention relates to an improved reactor for propane oxidation while in another aspect, the invention relates to an improved process for propane oxidation.

2. Description of the Related Art

In the direct oxidation of propane to acrylic acid (AA) process, propionic acid (PA) is formed as an undesirable side product. In one embodiment of the propane to AA process, the preferred catalyst system consists of mixed metal oxides of molybdenum, vanadium, tellurium and niobium (Mo/V/Te/Nb). These catalysts produce PA at levels that may range from over 1,000 parts per million (ppm) to less than 10,000 ppm when operating under conditions to achieve maximum AA yield (equal to or greater than ($\geq$) 85% oxygen conversion).

In addition, excess propionic acid byproduct can, upon esterification of the AA product, impart undesirable characteristics such as high volatile organic content (VOC), odor or color to the acrylate ester (AE) and its corresponding polymer products. Typically, PA specifications for AA product streams from conventional propylene oxidation, prior to esterification, range from 500-1000 ppm, well below the levels seen in the propane oxidation product. Thus, in order for propane oxidation to be more economically desirable, PA byproduct levels need to be reduced either through the oxidation step or in downstream separation steps.

The separation of propionic acid from acrylic acid is problematic. The boiling points of both are less than ($<$) 1° C. apart, and they are not capable of separation by distillation. Although methods exist for PA separation, e.g., melt crystallization, these steps substantially increase the capital and operating cost of the AA purification process by requiring additional equipment and utilities to effect the desired separation. Thus it would be advantageous and desirable to be able to control the AA process in such a way as to reduce the formation of PA such that additional costly purification is substantially reduced.

SUMMARY OF THE INVENTION

In one embodiment the invention is the use of oxidation reactors with improved heat transfer and length/diameter (L/D) ratios to reduce PA yields in propane oxidation. Reactors which have a lower temperature difference between reactor set point and peak temperature and/or are packed to maximize the L/D ratio produce AA with significantly reduced levels of PA byproduct as compared to reactors operated at similar conditions and using the same catalyst but in which the temperature difference and/or L/D ratio are not optimized.

In one embodiment the invention is a reactor packed with an active catalyst for the direct oxidation of propane to acrylic acid, the catalyst packed in the reactor such that the effective L/D ratio of the reactor is greater than ($>$) ten, preferably from 20 to 40.

In one embodiment the invention is a process for the direct oxidation of propane to acrylic acid, the process comprising the step of contacting under oxidation conditions propane and oxygen with a propane oxidation catalyst, the oxidation conditions comprising a set point temperature and a peak temperature with a temperature difference ($\Delta T$) between the set point and peak temperature of less than 20° C.

In one embodiment the invention is a process for the direct oxidation of propane to acrylic acid, the process comprising the step of contacting under oxidation conditions propane and oxygen with a propane oxidation catalyst, the oxidation catalyst packed in a reactor such that the effective L/D ratio of the reactor is $>10$ and the oxidation conditions comprising a set point temperature and a peak temperature with a $\Delta T$ between the set point and peak temperatures of less than 20° C.

DETAILED DESCRIPTION OF THE PREFERRED EMBODIMENT

Definitions

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, etc., is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the oxidation conditions of the process, PA content in AA streams, and the like.

Process Reactants

The starting materials are generally propane gas, at least one oxygen-containing gas, steam and a diluent gas. The propane does not have to meet any particularly high purity standard, and it may contain propylene or other hydrocarbons or heteroatom-containing hydrocarbons as impurities. In one embodiment the propane does not contain any appreciable amount of propylene, e.g., less than 1, or less than 0.5, or less than 0.1, wt % propylene based on the weight of the propane. In one embodiment the propane contains a relatively large amount, e.g., 1 or more wt %, of propene such as that found in lower-grade propane feeds such as those from fluid catalytic crackers.

The oxygen-containing gases used in the practice of this invention may be pure oxygen gas, an oxygen-containing gas such as air, an oxygen-enriched gas, or a mixture comprising two or more of these gases. The diluent gas is typically an inert gas such as but not limited to nitrogen, argon, helium, and carbon dioxide. The diluting gas may be used to dilute the starting material and/or to adjust the space velocity, the oxygen partial pressure, and the steam partial pressure. Each of these gases may be added to the process individually or in combination with one or more of the other gases.

In one embodiment the propane can be supplemented or replaced with another alkane suitable for gas phase oxidation into an unsaturated aldehyde or carboxylic acid. Generally, the alkane other than propane is a $C_{4-8}$ alkane, typically isobutane or n-butane. Like propane, these other alkanes do not have to meet any particularly high purity standard, and these may contain one or more $C_{3-8}$ alkenes as an impurity. Typical alkenes include propene, isobutene, n-butene, pentene, and the like.

In one embodiment a $C_{3-8}$ alkene feed replaces the propane, and this alkene feed may contain a significant amount of alkane, e.g. up to 49 weight percent (wt %). In one embodiment the feed is isobutene.

Suitable molar ratios of the propane/oxygen/diluting gas/water in the starting material gas mixture are known in the art as well as the feed ratio of propane/air/steam. For instance suitable ranges are disclosed in U.S. Pat. No. 5,380,933. Typical ranges include propane to oxygen to water to diluent of 1:(0.1-10):(0-50):(0-50), more typically 1:(0.5-5):(1-30):(0-30). In one embodiment the starting gas mixture comprises from 5 to 10, or from 6 to 8, weight percent (wt %) propane; from 10 to 20 wt % oxygen; from 1 to 50 wt % steam; and the balance nitrogen.

Process Conditions

The starting gas mixture is subjected to catalytic oxidation in the presence of an oxidation catalyst. The reaction is generally conducted under atmospheric pressure, but may be conducted under elevated or reduced pressure. Typically the reaction pressure is from 0 to 100, more typically from 0 to 50 pounds per square inch gauge (psig) (0 to 0.70MegaPascals (MPa), more typically 0 to 0.35 MPa). The reaction temperature is generally from 0° C. to 550° C., more typically from 200° C. to 500° C., even more typically from 300° C. to 480° C. and even more typically from 350° C. to 440° C. The gas space velocity is generally 100 to 10,000 hr$^{-1}$ more typically 300 to 6,000 hr$^{-1}$ and even more typically 300 to 3,000 hr$^{-1}$. Residence time of the starting gas mixture in the reactor is typically from 0.1 to 10 seconds, more typically from 1 to 4 seconds.

Oxidation Catalyst

The oxidation catalysts used in the practice of this invention are mixed metal oxides. The composition of the catalyst can vary widely and any of the catalysts known in the art for the oxidation of an alkane to an unsaturated aldehyde and/or carboxylic acid can be employed. Representative of these catalysts are those of Formula I

$$Mo_1V_bM^1{}_cM^2{}_dO_n \quad (I)$$

where $M_1$ is Te and/or Sb, $M_2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, d is from >0 to 1 and n is a number which is determined by the valences and frequency of the elements other than oxygen in (I). In one embodiment $M^1$ is Te and $M^2$ is Nb. The catalysts can be supported or unsupported, and they can be prepared by any one of a number of know procedures using known and commercially available equipment (see, for example, U.S. Pat. No. 6,180,825). Typical supports include silica, alumina, titania, aluminosilicate, diatomaceous earth and zirconium. Catalyst shape and catalyst particle size can vary to convenience.

Reactor

Typically oxidation catalyst is tightly packed into the tube and held in place by a porous plug or stopper at or near each end of the tube. The plugs are porous to the starting gas mixture and/or the gaseous products of the oxidation reaction. The catalyst is packed in a manner that allows the starting gas mixture to flow over and around the catalyst particles under oxidation conditions so as to convert the propane to acrylic acid. Typically, a commercial process will employ more than one tube reactor at a time, and these are typically grouped or welded into a single housing through which a heat transfer fluid is passed between and about the tubes to maintain a uniform temperature throughout the housing and in each tube. The reaction is exothermic and, as such, releases heat. The heat transfer fluid is used to remove heat and avoid the formation of hot spots which may adversely affect the catalyst. Suitable heat transfer media include inorganic salts and the DOWTHERM™ products. The reactor may consist of a single reactor stage, multiple reactor stages in separate reactor shells or multiple reactor stages in a single reactor shell. The optimum number of reactor stages is chosen to maximize the yield of AA while maintaining an economical capital and operating cost.

The reactor has an L/D ratio of >10, preferably from 20 to 40. This ratio can be achieved in any one of a number of ways including tube configuration and/or the use of diluents in the catalyst packing. For example, an oxidation catalyst can be mixed with one or more inert solids, e.g., clay, silica, polymeric granules or beads, so that the effective L/D of the tube reactor is increased by 10, 20, 30, 40, 50 or more percent.

The reactor is isothermally very efficient, i.e., it maintains a relatively uniform reaction temperature over its volume. "Relatively uniform reaction temperature" and like terms mean that the temperature difference (ΔT) between the reactor set point temperature and the peak temperature is 20° C. or less. "Reactor set point temperature" is the target temperature for the oxidation reaction, i.e., the temperature at which the bulk of the reaction is designed to occur, and it typically excludes the ramp up and cool down temperatures at the beginning and end of the reaction, respectively. "Peak temperature" is the temperature recorded at the hottest point along the catalyst bed measured periodically over the course of the reaction run. Peak temperatures typically are the result of hot spots in the catalyst bed or packing as opposed to a uniform temperature across the catalyst bed.

ΔT can be measured by any of the methods known to those skilled in the art. In one embodiment a reactor set point temperature is measured by a thermocouple placed within a cavity of the furnace, e.g., between an outer shell and reactor tube, and the peak temperature is measured by a thermocouple placed within the catalyst bed. The ΔT is simply the difference between the two recorded temperatures. The ΔT can be determined intermittently or continuously.

Specific Embodiments

The catalyst(s) used in these examples was a high-performance Mo/V/Te/Nb mixed metal oxide prepared according to the procedure described in U.S. Pat. No. 7,304,014. The process examples below are runs taken at similar conditions and compared at constant oxygen conversion.

EXAMPLE 1

An undiluted catalyst charge (4.0 cc) is loaded into a 0.25 inch OD 316 SS tube encased by a 1 inch diameter brass jacket to help ensure isothermal heat transfer. A first thermocouple is located in the annular space between the reactor tube and brass jacket to monitor the reactor set point temperature. A second thermocouple is included within the catalyst charge. The second thermocouple runs most of the length of the catalyst bed, and records a number of temperatures over the length of the bed. The highest recorded temperature at any moment in time is the peak temperature at that moment.

The feed composition in weight percent is 6.0% propane, 11.3% oxygen, 20% steam, with nitrogen as the balance. Residence time is 3.0 seconds at atmospheric pressure. Reactor temperatures are adjusted to give the desired conversion. Gas and liquid products are analyzed by gas chromotography (GC).

Comparative Example 1

A similar catalyst (also 4.0 cc) is diluted 1:1 with inert diluent and then loaded into a 0.5 inch OD SS tube. The reaction is processed with the following feed composition in wt %: 7.0% propane, 14.7% oxygen, 23% steam, with nitrogen as the balance. Residence time was 3.0 seconds at atmospheric pressure. Reactor temperatures are adjusted to give the desired conversion. Gas and liquid products are analyzed by GC.

The results from the two runs are reported in the following table. The difference in the feed compositions is not significant as the feed ratios are very close to one another. Of significance is the reduction in PA at similar AA yields and oxygen conversions. The data clearly shows that a reduction in PA of >35% is achieved in the run using the L/D and ΔT parameters of the invention.

TABLE

Reaction Conditions and Results of Ex. 1 and Comp. Ex. 1

| | Steam level, % | $O_2$ conv, % | AA yield, % | PA, ppm | L/D | ΔT, °C. |
|---|---|---|---|---|---|---|
| Example 1 | 20 | 77.0 | 42.4 | 950 | 33 | 2 |
| Comp. Example 1 | 22-23 | 77.0 | 44.0 | 1500 | 8 | 42 |

Although the invention has been described with certain detail through the preceding description of the preferred embodiments, this detail is for the primary purpose of illustration. Many variations and modifications can be made by one skilled in the art without departing from the spirit and scope of the invention as described in the following claims.

What is claimed is:

1. A process for the direct oxidation of propane to acrylic acid, the process comprising the step of contacting under oxidation conditions propane and oxygen with a propane oxidation catalyst, the oxidation catalyst packed in a tubular reactor such that the effective L/D ratio of the reactor is from 20 to 40 and the oxidation conditions comprising a reactor set point temperature and a peak temperature with a ΔT between the set point and peak temperatures of less than 20° C. wherein the reactor set point temperature is the target temperature for the oxidation of propane to acrylic acid.

2. The process of claim 1 in which the propane contains less than 0.5 wt % propylene based on the weight of the propane.

3. The process of claim 1 in which the propane oxidation catalyst is mixed with one or more inert solids.

4. The process of claim 1, in which the propane catalyst is a Mo/V/Te/Nb mixed metal oxide.

5. The process of claim 4, wherein the set point temperature is from 200° C. to 500° C.

* * * * *